(12) United States Patent
Yanev et al.

(10) Patent No.: US 11,064,910 B2
(45) Date of Patent: Jul. 20, 2021

(54) PHYSICAL ACTIVITY MONITORING SYSTEM

(75) Inventors: Kostadin Dimitrov Yanev, Alamo, CA (US); Asen Angelov Marinov, Redwood City, CA (US); Angel Marinov Angelov, Redwood City, CA (US)

(73) Assignee: ACTIVBODY, INC., San Diego, CA (US)

( * ) Notice: Subject to any disclaimer, the term of this patent is extended or adjusted under 35 U.S.C. 154(b) by 0 days.

(21) Appl. No.: 12/963,522

(22) Filed: Dec. 8, 2010

(65) Prior Publication Data

US 2012/0150074 A1 Jun. 14, 2012

(51) Int. Cl.
*A61B 5/11* (2006.01)
*A43B 3/00* (2006.01)
(Continued)

(52) U.S. Cl.
CPC .......... *A61B 5/1107* (2013.01); *A43B 3/0005* (2013.01); *A61B 5/222* (2013.01);
(Continued)

(58) Field of Classification Search
CPC ..... A61B 5/224; A61B 5/1118; A61B 5/6807; A61B 5/1107; A61B 2562/08;
(Continued)

(56) References Cited

U.S. PATENT DOCUMENTS

| 4,577,625 A | 3/1986 | Lohati et al. ............ 128/57 |
| 4,702,108 A | 10/1987 | Amundsen |

(Continued)

FOREIGN PATENT DOCUMENTS

| CN | 201270095 | 8/2009 |
| EP | 2284646 A1 | 2/2011 |

(Continued)

OTHER PUBLICATIONS

"Fitness Made Fun", WiiFit™, Instruction Booklet, copyright 2008 Nintendo, 28 pages.

(Continued)

*Primary Examiner* — Devin B Henson
*Assistant Examiner* — H. Q. Nguyen
(74) *Attorney, Agent, or Firm* — Pillsbury Winthrop Shaw Pittman LLP

(57) ABSTRACT

An exercise system may be configured to gather and quantify data related to energy expenditure during physical activity. The exercise system may include at least one force sensing node and a portable hub that is physically separate and distinct from the at least one force sensing node. The at least one force sensing node may be configured to gather data related to energy expenditure during physical activity. The portable hub may be configured to quantify data related to energy expended during physical activity. For example, according to exemplary implementations, the portable hub may be include a processor configured to execute an exercise analysis module. The exercise analysis module may be configured to determine one or more exercise parameters based on an output signal generated at the at least one force sensing node responsive to force exerted on the at least one force sensing node during physical activity.

14 Claims, 2 Drawing Sheets

(51) Int. Cl.
  *A61B 5/22* (2006.01)
  *A61B 5/103* (2006.01)
  *G16H 20/30* (2018.01)
  *A61B 5/00* (2006.01)

(52) U.S. Cl.
  CPC ............ *A61B 5/224* (2013.01); *A61B 5/6806* (2013.01); *A61B 5/6807* (2013.01); *A61B 5/1038* (2013.01); *A61B 5/1112* (2013.01); *A61B 2562/08* (2013.01); *G16H 20/30* (2018.01)

(58) Field of Classification Search
  CPC ...... A61B 5/1038; A61B 5/0022–0024; A43B 3/0005
  USPC .............. 600/595, 592, 300, 587, 586, 301; 701/410; 705/2
  See application file for complete search history.

(56) References Cited

U.S. PATENT DOCUMENTS

| | | | |
|---|---|---|---|
| 4,824,103 A | 4/1989 | Smidt | 272/125 |
| 4,988,981 A | 1/1991 | Zimmerman | |
| 5,144,284 A | 9/1992 | Hammett | |
| 5,242,348 A | 9/1993 | Bates | 482/105 |
| 5,471,405 A | 11/1995 | Marsh | 364/556 |
| 5,702,323 A | 12/1997 | Poulton | |
| 5,720,711 A | 2/1998 | Bond | |
| 5,790,102 A | 8/1998 | Nassimi | |
| 5,792,080 A | 8/1998 | Ookawa et al. | 601/115 |
| 5,890,995 A | 4/1999 | Bobick et al. | 482/4 |
| 5,904,639 A | 5/1999 | Smyser et al. | 482/91 |
| 5,923,318 A | 7/1999 | Zhai | |
| 5,982,342 A | 11/1999 | Iwata | |
| 5,997,489 A | 12/1999 | Iwamoto et al. | 601/73 |
| 6,013,007 A | 1/2000 | Root et al. | 482/8 |
| 6,063,045 A | 5/2000 | Wax | |
| 6,126,572 A | 10/2000 | Smith | 482/4 |
| 6,183,425 B1 | 2/2001 | Whalen et al. | 600/592 |
| 6,191,773 B1 | 2/2001 | Maruno | |
| 6,222,465 B1 | 4/2001 | Kumar | |
| 6,227,968 B1 | 5/2001 | Suzuki et al. | 463/7 |
| 6,324,557 B1 | 11/2001 | Chan | |
| 6,359,611 B2 | 3/2002 | Chan | |
| 6,360,597 B1 | 3/2002 | Hubbard, Jr. | 73/172 |
| 6,405,278 B1 | 6/2002 | Liepe | 711/103 |
| 6,435,937 B1 | 8/2002 | Naegele | |
| 6,513,532 B2* | 2/2003 | Mault et al. | 600/595 |
| 6,585,668 B2 | 7/2003 | Nissim | |
| 6,595,901 B2 | 7/2003 | Reinbold et al. | 482/91 |
| 6,597,347 B1 | 7/2003 | Yasutake | |
| 6,605,038 B1 | 8/2003 | Teller et al. | 600/300 |
| 6,616,579 B1 | 9/2003 | Reinbold et al. | 482/91 |
| 6,662,651 B1 | 12/2003 | Roth | |
| 6,675,130 B2 | 1/2004 | Kanevsky et al. | 702/188 |
| 6,776,345 B1 | 8/2004 | Liang | 235/486 |
| 6,807,869 B2 | 10/2004 | Farringdon et al. | 73/862.046 |
| 6,837,827 B1 | 1/2005 | Lee et al. | 482/8 |
| 6,914,695 B2 | 7/2005 | Walters et al. | 358/1.15 |
| 6,956,833 B1 | 10/2005 | Yukie et al. | 370/328 |
| 6,975,644 B2 | 12/2005 | Tordera et al. | 370/463 |
| 7,026,940 B2 | 4/2006 | Cherubini | |
| 7,121,982 B2 | 10/2006 | Feldman | |
| 7,161,490 B2 | 1/2007 | Huiban | |
| 7,169,120 B2 | 1/2007 | Murdock et al. | 601/129 |
| 7,171,331 B2* | 1/2007 | Vock | A43B 3/00 702/160 |
| 7,192,387 B2 | 3/2007 | Mendel | |
| 7,229,385 B2 | 6/2007 | Freeman et al. | 482/4 |
| 7,292,867 B2 | 11/2007 | Werner et al. | 455/456.3 |
| 7,303,534 B2 | 12/2007 | Kahn | 600/587 |
| 7,398,151 B1 | 7/2008 | Burrell et al. | 701/200 |
| 7,400,257 B2* | 7/2008 | Rivas | G08B 21/0211 340/573.1 |
| 7,429,251 B2 | 9/2008 | Tanizawa et al. | 601/94 |
| 7,468,968 B2 | 12/2008 | Svensson et al. | 370/338 |
| 7,480,512 B2 | 1/2009 | Graham et al. | 455/456.3 |
| 7,499,746 B2 | 3/2009 | Buhlmann et al. | 607/2 |
| 7,517,327 B1 | 4/2009 | Knight | 601/46 |
| 7,526,314 B2 | 4/2009 | Kennedy | 455/556.1 |
| 7,526,954 B2 | 5/2009 | Haselhurst et al. | 73/172 |
| RE40,891 E | 9/2009 | Yasutake | |
| 7,643,895 B2 | 1/2010 | Gupta et al. | 700/94 |
| 7,666,118 B1 | 2/2010 | Anthony | |
| 7,699,755 B2 | 4/2010 | Feldman | |
| 7,699,757 B2 | 4/2010 | Clem et al. | 482/49 |
| 7,702,821 B2 | 4/2010 | Feinberg et al. | 710/13 |
| 7,717,825 B2 | 5/2010 | Van Der Hoeven | |
| 7,758,469 B2 | 7/2010 | Dyer et al. | 482/4 |
| 7,789,800 B1 | 9/2010 | Watterson et al. | 482/8 |
| 7,840,346 B2 | 11/2010 | Huhtala | |
| 7,909,741 B2 | 3/2011 | Kim | |
| 7,921,716 B2* | 4/2011 | Morris Bamberg | A43B 3/0005 73/379.05 |
| 7,975,543 B2 | 7/2011 | Clem | |
| 8,009,056 B2 | 8/2011 | Greene | |
| 8,025,606 B2 | 9/2011 | Hamilton | |
| 8,027,822 B2 | 9/2011 | Turgiss et al. | 703/11 |
| 8,172,723 B1 | 5/2012 | Yanev et al. | 482/8 |
| 8,200,323 B2 | 6/2012 | DiBenedetto | |
| 8,203,454 B2 | 6/2012 | Knight | |
| 8,255,079 B2* | 8/2012 | Linn | B25J 9/0006 482/47 |
| 8,287,434 B2 | 10/2012 | Zavadsky | |
| 8,343,013 B1 | 1/2013 | Yanev et al. | 482/8 |
| 8,491,446 B2 | 7/2013 | Hinds | |
| 8,618,400 B2 | 12/2013 | Murphy | |
| 8,935,438 B1 | 1/2015 | Ivanchenko | |
| 2001/0049470 A1 | 12/2001 | Mault et al. | 600/300 |
| 2002/0146670 A1 | 10/2002 | Selles et al. | 434/247 |
| 2003/0020629 A1 | 1/2003 | Swartz | |
| 2003/0040688 A1 | 2/2003 | Bauer | 601/23 |
| 2003/0093012 A1 | 5/2003 | Smyser | |
| 2003/0097878 A1 | 5/2003 | Farringdon et al. | |
| 2003/0137495 A1 | 7/2003 | Canova | |
| 2004/0021681 A1 | 2/2004 | Liao | 345/702 |
| 2004/0058305 A1 | 3/2004 | Lurie | |
| 2004/0110602 A1 | 6/2004 | Feldman | |
| 2004/0176226 A1 | 9/2004 | Carlson | |
| 2004/0260215 A1 | 12/2004 | Kim | 601/99 |
| 2005/0040999 A1 | 2/2005 | Numano | |
| 2005/0130742 A1 | 6/2005 | Feldman | |
| 2005/0177054 A1 | 8/2005 | Yi | |
| 2005/0209049 A1 | 9/2005 | Shields | |
| 2005/0219355 A1 | 10/2005 | Tahara | |
| 2005/0283204 A1 | 12/2005 | Buhlmann | |
| 2006/0035762 A1 | 2/2006 | Smyser | |
| 2006/0064042 A1 | 3/2006 | Smyser | |
| 2006/0100899 A1 | 5/2006 | Tajima | 705/2 |
| 2006/0122819 A1 | 6/2006 | Carmel | |
| 2006/0247095 A1 | 11/2006 | Rummerfield | |
| 2007/0155589 A1 | 1/2007 | Shimizu | |
| 2007/0024736 A1 | 2/2007 | Matsuda | |
| 2007/0051842 A1 | 3/2007 | Pryor | 242/378.3 |
| 2007/0184953 A1 | 8/2007 | Luberski | |
| 2007/0219059 A1 | 9/2007 | Schwartz et al. | 482/8 |
| 2007/0219469 A1 | 9/2007 | Vardy | |
| 2007/0232455 A1 | 10/2007 | Hanoun | |
| 2007/0249975 A1 | 10/2007 | Pan et al. | 601/118 |
| 2007/0270727 A1 | 11/2007 | Khorassanizadeh | |
| 2008/0090703 A1 | 4/2008 | Rosenberg | 492/8 |
| 2008/0091762 A1 | 4/2008 | Neuhauser et al. | 709/201 |
| 2008/0096726 A1 | 4/2008 | Riley et al. | 482/8 |
| 2008/0100718 A1 | 5/2008 | Louks et al. | 348/211.2 |
| 2008/0101272 A1 | 5/2008 | Hayes et al. | 370/313 |
| 2008/0132388 A1 | 6/2008 | Clem | |
| 2008/0146336 A1 | 6/2008 | Feldman et al. | 463/37 |
| 2008/0161051 A1 | 7/2008 | Schobbert et al. | 455/558 |
| 2008/0164979 A1 | 7/2008 | Otto | |
| 2008/0171311 A1 | 7/2008 | Centen | |
| 2008/0261696 A1 | 10/2008 | Yamazaki | |
| 2008/0262918 A1 | 10/2008 | Wiener | 705/14 |

(56) References Cited

U.S. PATENT DOCUMENTS

| | | | |
|---|---|---|---|
| 2008/0281234 A1* | 11/2008 | Goris et al. .................. | 600/595 |
| 2008/0287832 A1 | 11/2008 | Collins et al. ............... | 600/587 |
| 2008/0300055 A1 | 12/2008 | Lutnick | |
| 2008/0319661 A1* | 12/2008 | Werner ............. | A63B 24/0062 |
| | | | 455/456.3 |
| 2009/0017993 A1 | 1/2009 | Khanicheh | |
| 2009/0025475 A1 | 1/2009 | DeBeliso | |
| 2009/0035740 A1 | 2/2009 | Reed | |
| 2009/0048021 A1 | 2/2009 | Lian | |
| 2009/0048070 A1 | 2/2009 | Vincent et al. .................. | 482/8 |
| 2009/0069160 A1 | 3/2009 | Summers | |
| 2009/0076855 A1 | 3/2009 | McCord ......................... | 705/3 |
| 2009/0098980 A1 | 4/2009 | Waters | |
| 2009/0144080 A1 | 6/2009 | Gray et al. ........................ | 705/2 |
| 2009/0148821 A1 | 6/2009 | Carkner et al. ............... | 434/265 |
| 2009/0228068 A1 | 9/2009 | Buhlmann et al. ............. | 607/48 |
| 2009/0286654 A1 | 11/2009 | Rice | |
| 2010/0021876 A1 | 1/2010 | Clash | |
| 2010/0265179 A1 | 1/2010 | Ram | |
| 2010/0056341 A1 | 3/2010 | Ellis | |
| 2010/0069148 A1 | 3/2010 | Cargill ........................... | 463/25 |
| 2010/0087763 A1 | 4/2010 | Hane-Karr .................. | 601/137 |
| 2010/0127983 A1 | 5/2010 | Irani | |
| 2010/0137105 A1 | 6/2010 | McLaughlin | |
| 2010/0178981 A1 | 7/2010 | Holcomb | |
| 2010/0197462 A1 | 8/2010 | Piane | |
| 2010/0245239 A1 | 9/2010 | Sternberg | |
| 2010/0248822 A1 | 9/2010 | Migos | |
| 2010/0255862 A1 | 10/2010 | Mitsunaga | |
| 2010/0255957 A1 | 10/2010 | Clem | |
| 2010/0259472 A1 | 10/2010 | Radivojevic | |
| 2010/0273610 A1 | 10/2010 | Johnson | |
| 2010/0279825 A1 | 11/2010 | Riley | |
| 2010/0292050 A1 | 11/2010 | DiBenedetto et al. ........... | 482/9 |
| 2010/0292600 A1 | 11/2010 | DiBenedetto et al. ....... | 600/520 |
| 2011/0035303 A1 | 2/2011 | Jakstadt et al. ................. | 705/34 |
| 2011/0046687 A1 | 2/2011 | Naschberger | |
| 2011/0054359 A1* | 3/2011 | Sazonov ............. | A61B 5/4866 |
| | | | 600/595 |
| 2011/0086747 A1 | 4/2011 | Broderick | |
| 2011/0124470 A1 | 5/2011 | Spurling | |
| 2011/0125866 A1 | 5/2011 | Williams | |
| 2011/0143769 A1 | 6/2011 | Jones | |
| 2011/0149694 A1* | 6/2011 | Sakita .................... | A63B 69/12 |
| | | | 368/10 |
| 2011/0165998 A1 | 7/2011 | Lau | |
| 2011/0187660 A1 | 8/2011 | Hirata | |
| 2011/0251021 A1 | 10/2011 | Zavadsky et al. ............... | 482/5 |
| 2011/0260987 A1 | 10/2011 | Zhao et al. .................. | 345/173 |
| 2011/0291943 A1 | 12/2011 | Thorn et al. .................. | 345/173 |
| 2011/0302694 A1 | 12/2011 | Wang | |
| 2012/0041767 A1* | 2/2012 | Hoffman ............... | G06Q 50/22 |
| | | | 705/1.1 |
| 2012/0047465 A1 | 2/2012 | Noda | |
| 2012/0051596 A1 | 3/2012 | Darnell | |
| 2012/0058861 A1 | 3/2012 | Satut | |
| 2012/0066591 A1 | 3/2012 | Hackwell | |
| 2012/0071732 A1 | 3/2012 | Grey et al. .................... | 600/301 |
| 2012/0075236 A1 | 3/2012 | Kim | |
| 2012/0077163 A1 | 3/2012 | SucarSuccar | |
| 2012/0078113 A1 | 3/2012 | Whitestone | |
| 2012/0088553 A1 | 4/2012 | Nunes | |
| 2012/0098744 A1 | 4/2012 | Stinson | |
| 2012/0108394 A1 | 5/2012 | Jones | |
| 2012/0112922 A1 | 5/2012 | Hillis | |
| 2012/0113019 A1 | 5/2012 | Anderson | |
| 2012/0116550 A1 | 5/2012 | Hoffman et al. ............... | 700/91 |
| 2012/0126941 A1 | 5/2012 | Coggill | |
| 2012/0162080 A1 | 6/2012 | Cao ............................. | 345/168 |
| 2012/0260220 A1 | 10/2012 | Griffin | |
| 2012/0265112 A1 | 10/2012 | Chen ........................... | 601/115 |
| 2012/0274508 A1 | 11/2012 | Brown | |
| 2012/0306782 A1 | 12/2012 | Seo et al. .................... | 345/173 |
| 2013/0009907 A1 | 1/2013 | Rosenberg | |
| 2013/0059696 A1 | 3/2013 | Hijmans | |
| 2013/0072301 A1 | 3/2013 | Mallinson | |
| 2013/0076649 A1 | 3/2013 | Myers | |
| 2013/0093679 A1 | 4/2013 | Dickinson | |
| 2013/0106155 A1 | 5/2013 | Chang | |
| 2013/0127748 A1 | 5/2013 | Vertegaal | |
| 2013/0127980 A1 | 5/2013 | Haddick | |
| 2013/0201316 A1 | 8/2013 | Binder | |
| 2013/0212674 A1 | 8/2013 | Boger | |
| 2013/0337974 A1 | 12/2013 | Yanev et al. ...................... | 482/8 |
| 2013/0337975 A1 | 12/2013 | Yanev et al. ...................... | 482/8 |
| 2013/0337976 A1 | 12/2013 | Yanev et al. ...................... | 482/8 |
| 2013/0344919 A1 | 12/2013 | Kim | |
| 2013/0345608 A1 | 12/2013 | Ehrenreich | |
| 2014/0062682 A1 | 3/2014 | Birnbaum | |
| 2014/0123003 A1 | 5/2014 | Song | |
| 2014/0184496 A1 | 7/2014 | Gribetz | |
| 2014/0317722 A1 | 10/2014 | Tartz | |
| 2014/0333543 A1 | 11/2014 | Yanev | |
| 2014/0335494 A1 | 11/2014 | Yanev | |
| 2015/0015476 A1 | 1/2015 | Yanev | |
| 2015/0173993 A1 | 6/2015 | Walsh | |

FOREIGN PATENT DOCUMENTS

| | | |
|---|---|---|
| JP | 2006345990 | 12/2006 |
| JP | 2009142333 | 7/2009 |
| JP | 2010524094 | 7/2010 |
| JP | 2013172841 | 9/2013 |
| TW | 509566 | 1/1988 |
| TW | 201000175 A * | 1/2010 |
| TW | 201300098 | 1/2013 |
| TW | 201301215 | 1/2013 |
| WO | 2007025382 | 3/2007 |
| WO | 2007/062102 A1 | 5/2007 |
| WO | WO 2012/078718 | 6/2012 |
| WO | WO 2013/192071 | 12/2013 |
| WO | WO 2013/192079 | 12/2013 |
| WO | WO 2013/192084 | 12/2013 |
| WO | 2014018049 | 1/2014 |
| WO | 2014182729 | 11/2014 |
| WO | 2014182735 | 11/2014 |
| WO | 2015006411 | 1/2015 |
| WO | 2015006413 | 1/2015 |

OTHER PUBLICATIONS

Jovanov et al., "A Wireless Body Area Network of Intelligent Motion Sensors for Computer Assisted Physical Rehabilitation", *Journal of NeuroEngineering and Rehabilitation*, Mar. 1, 2005, vol. 2, No. 6, retrieved from URL: http://www.jneuroengrehab.com/content/2/1/6, retrieved on Apr. 2, 2012, 10 pages.

Halfbakery, 'Computer Mouse with Pressure Sensitive Button', printed from http://www.halfbakery.com/idea/Computer_20Mouse_20with_20pressure . . . ', Cord, May 10, 2005, printed Apr. 4, 2014, 3 pages.

International Search Report and Written Opinion dated Apr. 20, 2012 for corresponding International Patent Application No. PCT/US2011/063678 (7 pages).

International Search Report and Written Opinion dated Mar. 13, 2015 for corresponding International Patent Application No. PCT/US2014/037012, 9 pages.

International Search Report and Written Opinion dated Mar. 4, 2015 for corresponding International Patent Application No. PCT/US2014/037018, 9 pages.

International Search Report and Written Opinion dated Nov. 22, 2013 for corresponding International Patent Application No. PCT/US2013/046082 (7 pages).

International Search Report and Written Opinion dated Nov. 7, 2014 for corresponding International Patent Application No. PCT/EPUS2014/045899 (7 pages).

International Search Report and Written Opinion dated Oct. 1, 2013 for corresponding International Patent Application No. PCT/US2013/046096 (10 pages).

International Search Report and Written Opinion dated Oct. 2, 2013 for corresponding International Patent Application No. PCT/US2013/046118 (10 pages).

(56) References Cited

OTHER PUBLICATIONS

Intellectual Property Office India, Examination Report issued in Indian Application No. 1993/KOLNP/2013 dated Aug. 16, 2019, pp. 1-12.

* cited by examiner

PHYSICAL ACTIVITY MONITORING SYSTEM

FIELD OF THE INVENTION

The invention relates to an exercise system configured to gather and quantify data related to energy expenditure during physical activity based on one or more signals generated at one or more pressure sensing nodes associated with one or more body parts of a user, such as the user's hands and/or feet.

BACKGROUND OF THE INVENTION

Typically, energy expenditure during physical activity is determined based on a small number of quantified aspects of the physical activity and/or of an individual performing the physical activity. Those aspects may include, for example, duration of the physical activity, body weight of the individual, gender of the individual, heart rate of the individual, and/or age of the individual. As such, energy expenditure determined by conventional systems lacks accuracy as it is not based on sufficient direct measurements and is largely estimated based on generalized models.

SUMMARY

One aspect of the disclosure relates to an exercise system configured to gather and quantify data related to energy expenditure during physical activity, according to one or more implementations of the invention. The exercise system may include at least one force sensing node and/or a portable hub, which may be physically separate and distinct from the sensing node. The force sensing node may be configured to gather data related to energy expenditure during physical activity, while the portable hub may be configured to quantify data related to energy expended during physical activity.

In exemplary implementations, as described further herein, the force sensing node may be configured to be positioned at a user's foot and/or hand such that a force exerted by the user's foot and/or hand is determined by the force sensing node. Such a position may be achieved when the force sensing node is integrated with (e.g., permanently or removably) with a wearable item such as, for example, a shoe and/or a glove. Responsive to force being exerted by the user, the force sensing node may generate a signal and transmit the signal to the portable hub. The portable hub may receive the signal from the force sensing node and process the signal to determine one or more exercise parameters associated with physical activity. Examples of the exercise parameters may include, for example, calories burned during physical activity, duration of physical activity, magnitude of force exerted during physical activity, distance traveled during physical activity, altitude ascended during physical activity, comparative information associated with prior physical activity, and/or other exercise parameters.

In addition to the force sensing node and/or the portable hub, according to some implementations, the exercise system may include one or more of a computing platform, a user accessory, external resources, and/or other components, which may complement and/or include various functionalities attributed herein to the force sensing node and/or the portable hub. Components of the exercise system, such as the force sensing node, the portable hub, the computing platform, the user accessory, and/or the external resources, may be operatively linked via one or more electronic communication links. For example, such electronic communication links may be established, at least in part, via a wired or wireless network, which may include the Internet, WiFi, LAN, Bluetooth, and/or other communication means. It will be appreciated that this is not intended to be limiting, and that the scope of this disclosure includes implementations in which the force sensing node, the portable hub, the computing platform, the user accessory, and/or the external resources are operatively linked via some other communication media.

As mentioned above, the force sensing node may be configured to gather data related to energy expenditure during physical activity. The force sensing node may be integrated into at least one wearable item such that force exerted by at least one body part wearing the at least one wearable item is exerted on the force sensing node. Examples of wearable items may include footwear, handwear, and/or other wearable items. In one embodiment, the force sensing node is integrated into an insole. The insole may be configured to be received by a shoe such that force exerted by the bottom of a foot wearing the shoe is exerted on the force sensing node. The force sensing node may include one or more of at least one force sensor, node communications apparatus, a node identification sensor, a node power supply, one or more node processors, and/or other components.

The force sensor may be configured to generate a first output signal. The force sensor may generate the first output signal responsive to force being exerted by at least one body part of a user on the force sensing node during physical activity. The first output signal may include information related to force exerted on the force sensing node. Such information may include or be used to determine magnitude of force, duration of force, a force magnitude profile as a function of time, a quantity of compressive forces, and/or other information related to compressive force exerted on the force sensing node. The output signal generated by the force sensor may be received and/or utilized by one or more components of the exercise system, as described further herein. In some implementations, the force sensor may include an array of force sensors. However, other apparatus configured for force sensing are contemplated and within the scope of the invention.

The node communications apparatus may be configured to receive and/or transmit signals. For example, the node communications apparatus may be configured to transmit the first output signal generated by the force sensor. Signals may be transmitted to and/or received from other components of the exercise system such as the portable hub, the computing platform, the user accessory, the external resources, and/or other components. As such, the node communications apparatus may include a wired or wireless transmitter, a wired or wireless receiver, and/or a combined wired or wireless transmitter and receiver. In some implementations, the node communications apparatus may be configured to receive one or more of software updates, firmware updates, and/or other updates.

The node identification sensor may be configured to identify the force sensing node and/or one or more components of the exercise system such as the portable hub. According to some implementations, the node identification sensor may include a radio-frequency identification device (RFID) and/or other identification apparatus. Identifying the force sensing node may include indicating a body part associated with the force sensing node.

The node power supply may be configured to supply electrical power to one or more components of the force sensing node. By way of non-limiting example, the node power supply may include a battery, a capacitor, apparatus for receiving electrical power from an external source (e.g., a wall socket), and/or other power supplies. In some implementations, the node power supply may be rechargeable. In one implementation, the node power supply may be recharged via inductive charging.

The node processor(s) may be configured to provide information processing capabilities in the force sensing node. The node processor may be configured to execute one or more computer program modules. The one or more computer program modules may include one or more of a node sensor module, a node communications module, a data processing module, a node power management module, and/or other modules.

The node sensor module may be configured to receive signals (e.g., the first output signal) from the force sensor and/or other signals. In some implementations, the node sensor module may be configured to timestamp received signals or information included in received signals.

The node communications module may be configured to control the node communications apparatus to transmit and/or receive information. In some implementations, the node communications apparatus may be controlled to transmit and/or receive information related to personal exercise and/or other information. Such information may be transmitted to and/or received from other components of the exercise system such as the computing platform, the user accessory, the external resources, and/or other components.

The data processing module may be configured to condition the signals received by node sensor module (e.g., the first output signal). Such conditioning may include, for example, conversion between analog to digital, reformatting of signals, extraction of information from signals, and/or other signal conditioning procedures. The data processing module may condition signals prior to the signals being transmitted by the node communications module, according to some implementations.

The node power management module may be configured to manage power delivered by the node power supply to one or more components of the force sensing node. In some implementations, the node power management module may temporarily discontinue or reduce power being supplied to one or more components of the force sensing node when those component(s) are not currently in use, such as the force sensor, the node communications apparatus, the node identification sensor, the node processor, and/or other components. As such, the node power management module may extend the lifetime of the node power supply and/or an individual charge thereof.

As mentioned above, the portable hub may be configured to quantify data related to energy expended during physical activity. According to exemplary implementations, the portable hub may include a small (e.g., handheld) form factor. As such, the portable hub may be worn by a user such as, for example, on a belt, a waistband, a lanyard, and/or other method of wearing the portable hub. The portable hub may be carried by the user, for example, in a pocket, a purse, and/or other method of carrying the portable hub. The portable hub may include one or more of hub communications apparatus, a hub identification sensor, a hub geo-location sensor, a hub motion sensor, hub display apparatus, a hub user interface, a hub power supply, hub electronic storage, one or more hub processors, and/or other components.

The hub communications apparatus may be configured to receive and/or transmit signals. Signals may be transmitted to and/or received from other components of the exercise system such as the portable hub, the computing platform, the user accessory, the external resources, and/or other components. For example, the hub communications apparatus may be configured to receive the first output signal from the node communications apparatus. The hub communications apparatus may be configured to transmit information related to the one or more exercise parameters. As such, the hub communications apparatus may include a wired or wireless transmitter, a wired or wireless receiver, and/or a combined wired or wireless transmitter and receiver. In some implementations, the hub communications apparatus may be configured to receive one or more of software updates, firmware updates, and/or other updates.

The hub identification sensor may be configured to identify the force sensing node from other force sensing nodes that may be included in the exercise system. The hub identification sensor may identify the force sensing node in conjunction with the node identification sensor. In some implementations, the hub identification sensor may include a RFID reader and/or other identification apparatus. Identifying the force sensing node may include identifying a body part associated with the force sensing node.

The hub geo-location sensor may be configured to generate a second output signal related to a geo-location of the portable hub. The second output signal may be used to quantify one or more parameters of personal exercise. Such parameters may include speed, distance traveled, course of travel, and/or other parameters related to a geo-location of the portable hub. By way of non-limiting example, the hub geo-location sensor may include a GPS device and/or other device configured to generate signals related to geo-location.

The hub motion sensor may be configured to generate a third output signal related to a motion of the portable hub. The third output signal may be used to quantify one or more parameters of personal exercise. Such parameters may include acceleration, orientation, and/or other parameters related to a motion of the portable hub. The hub motion sensor may include, for example, an accelerometer, a MEMS device, and/or other device configured to generate signal related to motion.

The hub display apparatus may be configured to display, for presentation to a user, information related to the one or more exercise parameters and/or other information. Such information may be conveyed by images, icons, video, text, illumination of a light or LED, and/or other visual indicators. In some implementations, the hub display apparatus may be separate from the portable hub and communicatively coupled with the portable hub. The hub display apparatus may include one or more of a screen, an LED, and/or other apparatus configured to provide visual feedback to a user of the portable hub. According to some implementations, the hub display apparatus may include a touch screen configured to receive information from the user.

The hub user interface may be configured to receive information from the user and/or provide information to the user. As such, the hub user interface may include hardware and/or software to facilitate receiving information from the user and/or providing information to the user. Exemplary hardware may include one or more of buttons, dials, touch pads, switches, analog sticks, a keypad, and/or other hardware. In accordance with some implementations, some or all of the hub user interface may be provided to the user via the hub display apparatus. In implementations where the hub display apparatus includes a touch screen, the user may provide information to the hub user interface by manipulating the touch screen.

In some implementations, the hub user interface may be configured to present user configurable settings to the user. The hub user interface may be configured to receive selections from the user of values for the user configurable settings. One or more user configurable settings may impact the current activity of one or more components of the portable hub. By way of non-limiting example, the user configurable settings may active and/or deactivate one or more components of the portable hub, and/or may configure one or more aspects of operation of the portable hub. The user configurable settings may be related to personal exercise of a user of the portable hub. The user configurable settings may be provided to the hub processor. The user configurable settings may be provided to one or more processors of other component of the exercise system such as, for example, the computing platform.

The hub power supply may be configured to supply electrical power to one or more components of the portable hub. By way of non-limiting example, the hub power supply may include a battery, a capacitor, apparatus for receiving electrical power from an external source (e.g., a wall socket), and/or other power supplies. In some implementations, the hub power supply may be rechargeable. The hub power supply may be recharged via inductive charging. In one implementation, where the hub communications apparatus includes a USB port or other wired communications port, the hub communications apparatus may receive electrical power from a component of the exercise system and/or another source to recharge the hub power supply.

The hub electronic storage may be configured to store information related to one or more exercise parameters and/or other information. The electronic storage may comprise electronic storage media that electronically stores information.

The hub processor(s) may be configured to provide information processing capabilities in the portable hub. The hub processor may be configured to execute one or more computer program modules. The one or more computer program modules may include one or more of a hub communications module, a hub sensor module, an exercise analysis module, a hub display module, a clocking module, a calendaring module, a hub power management module, and/or other modules.

The hub communications module may be configured to control the hub communications apparatus to transmit and/or receive information. Such information may be transmitted to and/or received from other components of the exercise system such as the force sensing node, computing platform, the user accessory, the external resources, and/or other components. In some implementations, the hub communications apparatus may be controlled by the hub communications module to receive the first output signal (generated by the force sensor) from the node communications apparatus. Information related to the first output signal, physical activity of a user, and/or other information may be transmitted to the computing platform, in accordance with some implementations.

The hub sensor module may be configured to receive signals from one or more of the hub identification sensor, the hub geo-location sensor (e.g., the second output signal), the hub motion sensor (e.g., the third output signal), and/or other sensors included in the portable hub. In some implementations, the hub sensor module may be configured to time-stamp received signals or information included in received signals.

The exercise analysis module may be configured to determine one or more exercise parameters. Exercise parameters may be related to physical activity of a user of the portable hub. Some exercise parameters may be determined based on the first output signal generated by the force sensor of the force sensing node. Some exercise parameters may be determined based on the second output signal generated by the hub geo-location sensor. Some exercise parameters may be determined based on the third output signal generated by the hub motion sensor. The one or more exercise parameters may include, for example, magnitude of force exerted on the force sensing node, duration of force exerted on the force sensing node, a force magnitude profile as a function of time, a quantity of forces exerted on the force sensing node, completion level of a prescribed exercise routine, speed, acceleration, distance traveled, course of travel, and/or other information related to physical activity.

The hub display module may be configured to control the hub display apparatus. Control of the hub display apparatus may include directing the hub display apparatus to present information related to one or more exercise parameters, force exerted on the force sensing node, physical activity, and/or other information. Such information may be conveyed by images, icons, video, text, and/or other visual indicators. Information related to force exerted on the force sensing node may include magnitude of compressive force exerted on the force sensing node, duration of force exerted on the force sensing node, a force magnitude profile as a function of time, a quantity of forces exerted on the force sensing node, and/or other information related to force exerted on the force sensing node. Information related to physical activity may include information related to a prescribed exercise routine, a previously completed exercise routine, an exercise routing of an individual besides the user of the portable hub, speed, distance traveled, course of travel, and/or other information related to personal exercise. In some implementations, the hub display module may control the hub display apparatus to indicate an operational state of the force sensing node and/or the portable hub. Operational states may include "on", "off", "stand-by", and/or other operational states.

The clocking module may be configured to provide one or more clocking functions to the portable hub. Examples of clocking functions may include a clock function, a timer function, a stopwatch function, an occasion alarm function, and/or other clocking functions. The clocking functions provided by the clocking module may be presented to a user via the hub display apparatus and/or the hub user interface. Clocking functions may be manipulated via the hub user interface.

The calendaring module may be configured to provide calendaring functions to the portable hub. Examples of calendaring functions may include managing a calendar associated with the portable hub, managing calendar events, and/or other calendaring functions. The calendaring functions provided by the calendaring module may be presented to a user via the hub display apparatus and/or the hub user interface. Calendaring functions may be manipulated via the hub user interface.

The hub power management module may be configured to manage power delivered by the hub power supply to one or more components of the portable hub. In some implementations, the hub power management module may temporarily discontinue or reduce power being supplied to one or more components of the portable hub when those component(s) are not currently in use, such as hub communications apparatus, the hub identification sensor, the hub geo-location sensor, the hub motion sensor, the hub display apparatus, the hub user interface, the hub electronic storage, the hub processor, and/or other components. As such, the hub power management module may extend the lifetime of the hub power supply and/or an individual charge thereof.

The computing platform may be configured to communicatively couple to the portable hub and/or other components of the exercise system. The computing platform may be configured to receive, transmit, process, and/or store information related to one or more of physical activity, at least one exercise parameter, force exerted on the force sensing node, information stored by the hub electronic storage, information and/or signals related to one or more components of the force sensing node and/or the portable hub, and/or other information. Processing of such information may include analysis, historical tracking, sharing with one or more individuals other than a user of the portable hub, and/or other processing. The computing platform may be physically separate and distinct from the force sensing node and/or the portable hub. The computing platform may include one or more processors configured to execute computer program modules that provide the functionalities attributed herein to the computing platform. According to some implementations, the computing platform may include one or more of a personal computer, a laptop computer, a tablet computer, a Smart phone, a personal digital assistant (PDA), and/or other computing platforms.

The user accessory may be configured to communicatively couple to the force sensing node, the portable hub, and/or other components of the exercise system. The user accessory may be configured to convey information related to one or more of personal exercise, aspects of a user of the portable hub (e.g., heart rate, temperature, and/or other aspects), force exerted on the force sensing node, information associated with the portable hub, and/or other information. The user accessory may be physically separate and distinct from the force sensing node and/or the portable hub. In some implementations, the user accessory may include one or more of a heart rate monitor, a thermometer, a device that measures aspects of a user of the portable hub, a wired headset, a wireless headset, wired headphones, wireless headphones, a device that includes a display, and/or other accessories.

The external resources may include sources of information, hosts and/or providers of interactive content outside of the exercise system, external entities participating with the exercise system, and/or other resources. In some implementations, some or all of the functionality attributed herein to the external resources may be provided by resources included in the exercise system.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION

Figure 1:
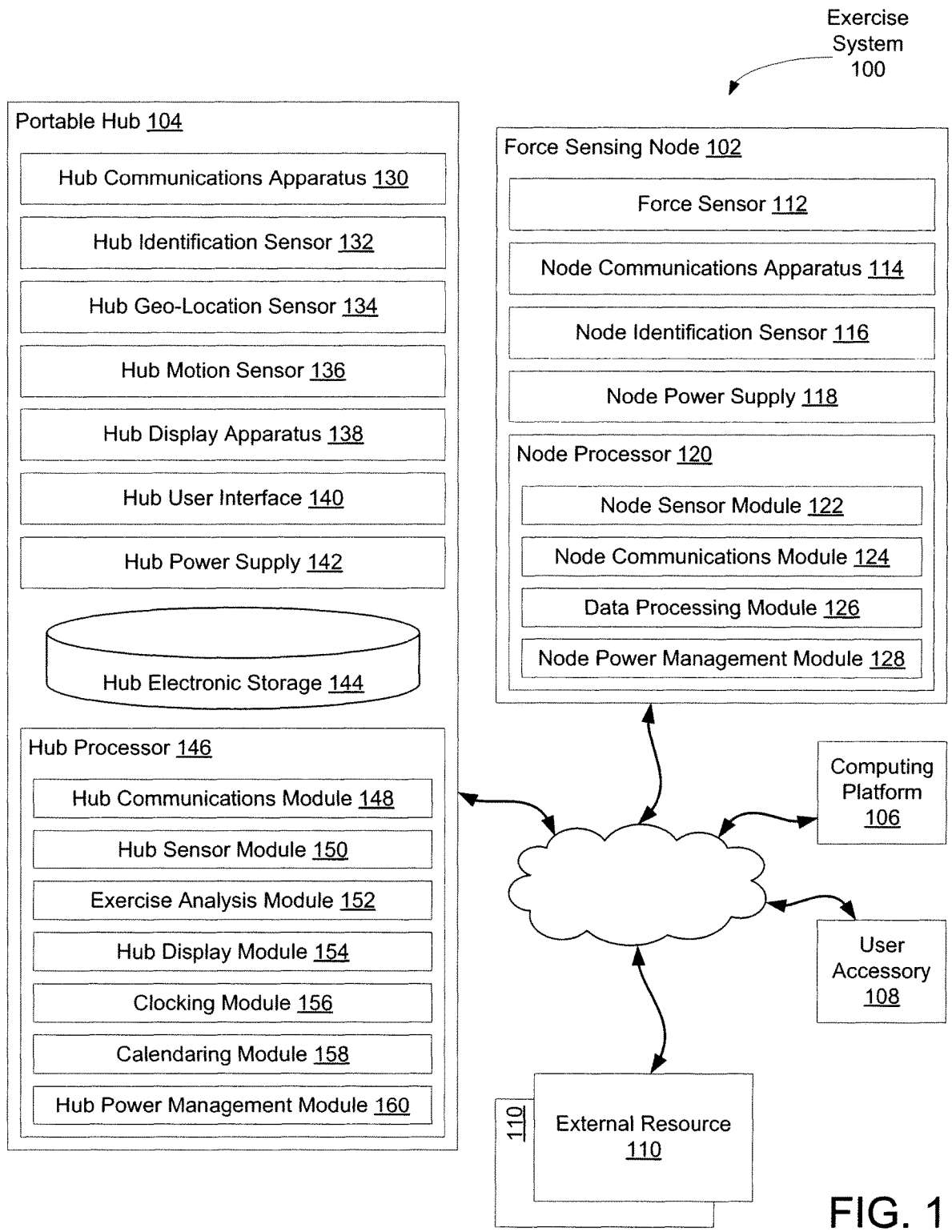
FIG. 1 illustrates an exercise system configured to gather and quantify data related to energy expenditure during physical activity, according to one or more implementations of the invention.

FIG. 1 illustrates an exercise system 100 configured to gather and quantify data related to energy expenditure during physical activity, according to one or more implementations of the invention. The exercise system 100 may include at least one force sensing node 102 and/or a portable hub 104, which may be physically separate and distinct from the sensing node 102. The force sensing node 102 may be configured to gather data related to energy expenditure during physical activity, while the portable hub 104 may be configured to quantify data related to energy expended during physical activity.

In exemplary implementations, as described further herein, the force sensing node 102 may configured to be positioned at a user's foot and/or hand such that a force exerted by the user's foot and/or hand is determined by the force sensing node 102. Such a position may be achieved when the force sensing node 102 is integrated with (e.g., permanently or removably) with a wearable item such as, for example, a shoe and/or a glove. Responsive to force being exerted by the user, the force sensing node 102 may generate a signal and transmit the signal to the portable hub 104. The portable hub 104 may receive the signal from the force sensing node 102 and process the signal to determine one or more exercise parameters associated with physical activity. Examples of the exercise parameters may include, for example, calories burned during physical activity, duration of physical activity, magnitude of force exerted during physical activity, distance traveled during physical activity, altitude ascended during physical activity, comparative information associated with prior physical activity, and/or other exercise parameters.

In addition to the force sensing node 102 and/or the portable hub 104, according to some implementations, the exercise system 100 may include one or more of a computing platform 106, a user accessory 108, external resources 110, and/or other components, which may complement and/or include various functionalities attributed herein to the force sensing node 102 and/or the portable hub 104. Components of the exercise system 100, such as the force sensing node 102, the portable hub 104, the computing platform 106, the user accessory 108, and/or the external resources 110, may be operatively linked via one or more electronic communication links. For example, such electronic communication links may be established, at least in part, via a wired or wireless network, which may include the Internet, WiFi, LAN, Bluetooth, and/or other communication means. It will be appreciated that this is not intended to be limiting, and that the scope of this disclosure includes implementations in which the force sensing node 102, the portable hub 104, the computing platform 106, the user accessory 108, and/or the external resources 110 are operatively linked via some other communication media.

As mentioned above, the force sensing node 102 may be configured to gather data related to energy expenditure during physical activity. The force sensing node 102 may be integrated into at least one wearable item such that force exerted by at least one body part wearing the at least one wearable item is exerted on the force sensing node 102. Examples of wearable items may include footwear, handwear, and/or other wearable items. In one embodiment, the force sensing node 102 is integrated into an insole. The insole may be configured to be received by a shoe such that force exerted by the bottom of a foot wearing the shoe is exerted on the force sensing node 102. As depicted in FIG. 1, the force sensing node 102 may include one or more of at least one force sensor 112, node communications apparatus 114, a node identification sensor 116, a node power supply 118, one or more node processors 120, and/or other components.

The force sensor 112 may be configured to generate a first output signal. The force sensor 112 may generate the first output signal responsive to force being exerted by at least one body part of a user on the force sensing node 102 during physical activity. The first output signal may include information related to force exerted on the force sensing node 102. Such information may include or be used to determine magnitude of force, duration of force, a force magnitude profile as a function of time, a quantity of compressive forces, and/or other information related to compressive force exerted on the force sensing node 102. The output signal generated by the force sensor 112 may be received and/or utilized by one or more components of the exercise system 100, as described further herein. By way of non-limiting example, the force sensor 112 may include a FlexiForce A201 force sensor from Tekscan, Inc. of South Boston, Mass. In some implementations, the force sensor 112 may include an array of force sensors. However, other apparatus configured for force sensing are contemplated and within the scope of the invention.

The node communications apparatus 114 may be configured to receive and/or transmit signals. For example, the node communications apparatus 114 may be configured to transmit the first output signal generated by the force sensor 112. Signals may be transmitted to and/or received from other components of the exercise system 100 such as the portable hub 104, the computing platform 106, the user accessory 108, the external resources 110, and/or other components. As such, the node communications apparatus 114 may include a wired or wireless transmitter, a wired or wireless receiver, and/or a combined wired or wireless transmitter and receiver. In some implementations, the node communications apparatus 114 may be configured to receive one or more of software updates, firmware updates, and/or other updates.

The node identification sensor 116 may be configured to identify the force sensing node 102 and/or one or more components of the exercise system 100 such as the portable hub 104. According to some implementations, the node identification sensor 116 may include a radio-frequency identification device (RFID) and/or other identification apparatus. Identifying the force sensing node 102 may include indicating a body part associated with the force sensing node 102.

The node power supply 118 may be configured to supply electrical power to one or more components of the force sensing node 102. By way of non-limiting example, the node power supply 118 may include a battery, a capacitor, apparatus for receiving electrical power from an external source (e.g., a wall socket), and/or other power supplies. In some implementations, the node power supply 118 may be rechargeable. In one implementation, the node power supply 118 may be recharged via inductive charging.

The node processor(s) 120 may be configured to provide information processing capabilities in the force sensing node 102. As such, the node processor 120 may include one or more of a digital processor, an analog processor, a digital circuit designed to process information, an analog circuit designed to process information, a state machine, and/or other mechanisms for electronically processing information. Although the node processor 120 is shown in FIG. 1 as a single entity, this is for illustrative purposes only. In some implementations, the node processor 120 may include a plurality of processing units. These processing units may be physically located within the same device, or the node processor 120 may represent processing functionality of a plurality of devices operating in coordination.

As is shown in FIG. 1, the node processor 120 may be configured to execute one or more computer program modules. The one or more computer program modules may include one or more of a node sensor module 122, a node communications module 124, a data processing module 126, a node power management module 128, and/or other modules. The node processor 120 may be configured to execute modules 122, 124, 126, and/or 128 by software; hardware; firmware; some combination of software, hardware, and/or firmware; and/or other mechanisms for configuring processing capabilities on the node processor 120.

It should be appreciated that although modules 122, 124, 126, and 128 are illustrated in FIG. 1 as being co-located within a single processing unit, in implementations in which the node processor 120 includes multiple processing units, one or more of modules 122, 124, 126, and/or 128 may be located remotely from the other modules. The description of the functionality provided by the different modules 122, 124, 126, and/or 128 described below is for illustrative purposes, and is not intended to be limiting, as any of modules 122, 124, 126, and/or 128 may provide more or less functionality than is described. For example, one or more of modules 122, 124, 126, and/or 128 may be eliminated, and some or all of its functionality may be provided by other ones of modules 122, 124, 126, and/or 128. As another example, the node processor 120 may be configured to execute one or more additional modules that may perform some or all of the functionality attributed below to one of modules 122, 124, 126, and/or 128.

The node sensor module 122 may be configured to receive signals (e.g., the first output signal) from the force sensor 112 and/or other signals. Signals received by the node sensor module 122 may be provided to one or more of modules 124, 126, and/or 128. In some implementations, the node sensor module 122 may be configured to timestamp received signals or information included in received signals.

The node communications module 124 may be configured to control the node communications apparatus 114 to transmit and/or receive information. In some implementations, the node communications apparatus 114 may be controlled to transmit and/or receive information related to personal exercise and/or other information. Such information may be transmitted to and/or received from other components of the exercise system 100 such as the computing platform 106, the user accessory 108, the external resources 110, and/or other components.

The data processing module 126 may be configured to condition the signals received by node sensor module 122 (e.g., the first output signal). Such conditioning may include, for example, conversion between analog to digital, reformatting of signals, extraction of information from signals, and/or other signal conditioning procedures. The data processing module 126 may condition signals prior to the signals being transmitted by the node communications module 124, according to some implementations.

The node power management module 128 may be configured to manage power delivered by the node power supply 118 to one or more components of the force sensing node 102. In some implementations, the node power management module 128 may temporarily discontinue or reduce power being supplied to one or more components of the force sensing node 102 when those component(s) are not currently in use, such as the force sensor 112, the node communications apparatus 114, the node identification sensor 116, the node processor 120, and/or other components. As such, the node power management module 128 may extend the lifetime of the node power supply 118 and/or an individual charge thereof.

As mentioned above, the portable hub 104 may be configured to quantify data related to energy expended during physical activity. According to exemplary implementations, the portable hub 104 may include a small (e.g., handheld) form factor. As such, the portable hub 104 may be worn by a user such as, for example, on a belt, a waistband, a lanyard, and/or other method of wearing the portable hub 104. The portable hub 104 may be carried by the user, for example, in a pocket, a purse, and/or other method of carrying the portable hub 104. As depicted in FIG. 1, the portable hub 104 may include one or more of hub communications apparatus 130, a hub identification sensor 132, a hub geo-location sensor 134, a hub motion sensor 136, hub display apparatus 138, a hub user interface 140, a hub power supply 142, hub electronic storage 144, one or more hub processors 146, and/or other components.

The hub communications apparatus 130 may be configured to receive and/or transmit signals. Signals may be transmitted to and/or received from other components of the exercise system 100 such as the portable hub 104, the computing platform 106, the user accessory 108, the external resources 110, and/or other components. For example, the hub communications apparatus 130 may be configured to receive the first output signal from the node communications apparatus 114. The hub communications apparatus 130 may be configured to transmit information related to the one or more exercise parameters. As such, the hub communications apparatus 130 may include a wired or wireless transmitter, a wired or wireless receiver, and/or a combined wired or wireless transmitter and receiver. In some implementations, the hub communications apparatus 130 may be configured to receive one or more of software updates, firmware updates, and/or other updates.

The hub identification sensor 132 may be configured to identify the force sensing node 102 from other force sensing nodes that may be included in the exercise system 100. The hub identification sensor 132 may identify the force sensing node 102 in conjunction with the node identification sensor 116. In some implementations, the hub identification sensor 132 may include a RFID reader and/or other identification apparatus. Identifying the force sensing node 102 may include identifying a body part associated with the force sensing node 102.

The hub geo-location sensor 134 may be configured to generate a second output signal related to a geo-location of the portable hub 104. The second output signal may be used to quantify one or more parameters of personal exercise. Such parameters may include speed, distance traveled, course of travel, and/or other parameters related to a geo-location of the portable hub 104. By way of non-limiting example, the hub geo-location sensor 134 may include a GPS device and/or other device configured to generate signals related to geo-location.

The hub motion sensor 136 may be configured to generate a third output signal related to a motion of the portable hub 104. The third output signal may be used to quantify one or more parameters of personal exercise. Such parameters may include acceleration, orientation, and/or other parameters related to a motion of the portable hub 104. The hub motion sensor 136 may include, for example, an accelerometer, a MEMS device, and/or other device configured to generate signal related to motion.

The hub display apparatus 138 may be configured to display, for presentation to a user, information related to the one or more exercise parameters and/or other information. Such information may be conveyed by images, icons, video, text, illumination of a light or LED, and/or other visual indicators. In some implementations, the hub display apparatus 138 may be separate from the portable hub 104 and communicatively coupled with the portable hub 104. The hub display apparatus 138 may include one or more of a screen, an LED, and/or other apparatus configured to provide visual feedback to a user of the portable hub 104. According to some implementations, the hub display apparatus 138 may include a touch screen configured to receive information from the user.

The hub user interface 140 may be configured to receive information from the user and/or provide information to the user. As such, the hub user interface 140 may include hardware and/or software to facilitate receiving information from the user and/or providing information to the user. Exemplary hardware may include one or more of buttons, dials, touch pads, switches, analog sticks, a keypad, and/or other hardware. In accordance with some implementations, some or all of the hub user interface 140 may be provided to the user via the hub display apparatus 138. In implementations where the hub display apparatus 138 includes a touch screen, the user may provide information to the hub user interface 140 by manipulating the touch screen.

In some implementations, the hub user interface 140 may be configured to present user configurable settings to the user. The hub user interface 140 may be configured to receive selections from the user of values for the user configurable settings. One or more user configurable settings may impact the current activity of one or more components of the portable hub 104. By way of non-limiting example, the user configurable settings may active and/or deactivate one or more components of the portable hub 104, and/or may configure one or more aspects of operation of the portable hub 104. The user configurable settings may be related to personal exercise of a user of the portable hub 104. The user configurable settings may be provided to the hub processor 146. The user configurable settings may be provided to one or more processors of other component of the exercise system 100 such as, for example, the computing platform 106.

The hub power supply 142 may be configured to supply electrical power to one or more components of the portable hub 104. By way of non-limiting example, the hub power supply 142 may include a battery, a capacitor, apparatus for receiving electrical power from an external source (e.g., a wall socket), and/or other power supplies. In some implementations, the hub power supply 142 may be rechargeable. The hub power supply 142 may be recharged via inductive charging. In one implementation, where the hub communications apparatus 130 includes a USB port or other wired communications port, the hub communications apparatus 130 may receive electrical power from a component of the exercise system 100 and/or another source to recharge the hub power supply 142.

The hub electronic storage 144 may be configured to store information related to one or more exercise parameters and/or other information. The electronic storage 144 may comprise electronic storage media that electronically stores information. The electronic storage media of the electronic storage 144 may include one or both of system storage that is provided integrally (i.e., substantially non-removable) with the portable hub 104 and/or removable storage that is removably connectable to the portable hub 104 via, for example, a port (e.g., a USB port, a firewire port, etc.) or a drive (e.g., a disk drive, etc.). The electronic storage 144 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. The electronic storage 144 may store software algorithms, information determined by the node processor 120 and/or the hub processor 146, information received from the computing platform 106, information received from the user accessory 108, information received from the external resources 110, and/or other information that enables the portable hub 104 to function as described herein.

The hub processor(s) 146 may be configured to provide information processing capabilities in the portable hub 104. As such, the hub processor 146 may include one or more of a digital processor, an analog processor, a digital circuit designed to process information, an analog circuit designed to process information, a state machine, and/or other mechanisms for electronically processing information. Although the hub processor 146 is shown in FIG. 1 as a single entity, this is for illustrative purposes only. In some implementations, the hub processor 146 may include a plurality of processing units. These processing units may be physically located within the same device, or the hub processor 146 may represent processing functionality of a plurality of devices operating in coordination.

As is shown in FIG. 1, the hub processor 146 may be configured to execute one or more computer program modules. The one or more computer program modules may include one or more of a hub communications module 148, a hub sensor module 150, an exercise analysis module 152, a hub display module 154, a clocking module 156, a calendaring module 158, a hub power management module 160, and/or other modules. The hub processor 146 may be configured to execute modules 148, 150, 152, 154, 156, 158, and/or 160 by software; hardware; firmware; some combination of software, hardware, and/or firmware; and/or other mechanisms for configuring processing capabilities on the hub processor 146.

It should be appreciated that although modules 148, 150, 152, 154, 156, 158, and 160 are illustrated in FIG. 1 as being co-located within a single processing unit, in implementations in which the hub processor 146 includes multiple processing units, one or more of modules 148, 150, 152, 154, 156, 158, and/or 160 may be located remotely from the other modules. The description of the functionality provided by the different modules 148, 150, 152, 154, 156, 158, and/or 160 described below is for illustrative purposes, and is not intended to be limiting, as any of modules 148, 150, 152, 154, 156, 158, and/or 160 may provide more or less functionality than is described. For example, one or more of modules 148, 150, 152, 154, 156, 158, and/or 160 may be eliminated, and some or all of its functionality may be provided by other ones of modules 148, 150, 152, 154, 156, 158, and/or 160. As another example, the hub processor 146 may be configured to execute one or more additional modules that may perform some or all of the functionality attributed below to one of modules 148, 150, 152, 154, 156, 158, and/or 160.

The hub communications module 148 may be configured to control the hub communications apparatus 130 to transmit and/or receive information. Such information may be transmitted to and/or received from other components of the exercise system 100 such as the force sensing node 102, computing platform 106, the user accessory 108, the external resources 110, and/or other components. In some implementations, the hub communications apparatus 130 may be controlled by the hub communications module 148 to receive the first output signal (generated by the force sensor 112) from the node communications apparatus 114. Information related to the first output signal, physical activity of a user, and/or other information may be transmitted to the computing platform 106, in accordance with some implementations.

The hub sensor module 150 may be configured to receive signals from one or more of the hub identification sensor 132, the hub geo-location sensor 134 (e.g., the second output signal), the hub motion sensor 136 (e.g., the third output signal), and/or other sensors included in the portable hub 104. Signals received by the hub sensor module 150 may be provided to one or more of modules 148, 152, 154, 156, 158, and/or 160. In some implementations, the hub sensor module 150 may be configured to timestamp received signals or information included in received signals.

The exercise analysis module 152 may be configured to determine one or more exercise parameters. Exercise parameters may be related to physical activity of a user of the portable hub 104. Some exercise parameters may be determined based on the first output signal generated by the force sensor 112 of the force sensing node 102. Some exercise parameters may be determined based on the second output signal generated by the hub geo-location sensor 134. Some exercise parameters may be determined based on the third output signal generated by the hub motion sensor 136. The one or more exercise parameters may include, for example, magnitude of force exerted on the force sensing node 102, duration of force exerted on the force sensing node 102, a force magnitude profile as a function of time, a quantity of forces exerted on the force sensing node 102, completion level of a prescribed exercise routine, speed, acceleration, distance traveled, course of travel, and/or other information related to physical activity.

The hub display module 154 may be configured to control the hub display apparatus 138. Control of the hub display apparatus 138 may include directing the hub display apparatus 138 to present information related to one or more exercise parameters, force exerted on the force sensing node 102, physical activity, and/or other information. Such information may be conveyed by images, icons, video, text, and/or other visual indicators. Information related to force exerted on the force sensing node 102 may include magnitude of compressive force exerted on the force sensing node 102, duration of force exerted on the force sensing node 102, a force magnitude profile as a function of time, a quantity of forces exerted on the force sensing node 102, and/or other information related to force exerted on the force sensing node 102. Information related to physical activity may include information related to a prescribed exercise routine, a previously completed exercise routine, an exercise routing of an individual besides the user of the portable hub 104, speed, distance traveled, course of travel, and/or other information related to personal exercise. In some implementations, the hub display module 154 may control the hub display apparatus 138 to indicate an operational state of the force sensing node 102 and/or the portable hub 104. Operational states may include "on", "off", "stand-by", and/or other operational states.

The clocking module 156 may be configured to provide one or more clocking functions to the portable hub 104. Examples of clocking functions may include a clock function, a timer function, a stopwatch function, an occasion alarm function, and/or other clocking functions. The clocking functions provided by the clocking module 156 may be presented to a user via the hub display apparatus 138 and/or the hub user interface 140. Clocking functions may be manipulated via the hub user interface 140.

The calendaring module 158 may be configured to provide calendaring functions to the portable hub 104. Examples of calendaring functions may include managing a calendar associated with the portable hub 104, managing calendar events, and/or other calendaring functions. The calendaring functions provided by the calendaring module 158 may be presented to a user via the hub display apparatus 138 and/or the hub user interface 140. Calendaring functions may be manipulated via the hub user interface 140.

The hub power management module 160 may be configured to manage power delivered by the hub power supply 142 to one or more components of the portable hub 104. In some implementations, the hub power management module 160 may temporarily discontinue or reduce power being supplied to one or more components of the portable hub 104 when those component(s) are not currently in use, such as hub communications apparatus 130, the hub identification sensor 132, the hub geo-location sensor 134, the hub motion sensor 136, the hub display apparatus 138, the hub user interface 140, the hub electronic storage 144, the hub processor 146, and/or other components. As such, the hub power management module 160 may extend the lifetime of the hub power supply 142 and/or an individual charge thereof.

The computing platform 106 may be configured to communicatively couple to the portable hub 104 and/or other components of the exercise system 100. The computing platform 106 may be configured to receive, transmit, process, and/or store information related to one or more of physical activity, at least one exercise parameter, force exerted on the force sensing node 102, information stored by the hub electronic storage 144, information and/or signals related to one or more components of the force sensing node 102 and/or the portable hub 104, and/or other information. Processing of such information may include analysis, historical tracking, sharing with one or more individuals other than a user of the portable hub 104, and/or other processing. The computing platform 106 may be physically separate and distinct from the force sensing node 102 and/or the portable hub 104. The computing platform 106 may include one or more processors configured to execute computer program modules that provide the functionalities attributed herein to the computing platform 106. According to some implementations, the computing platform 106 may include one or more of a personal computer, a laptop computer, a tablet computer, a Smart phone, a personal digital assistant (PDA), and/or other computing platforms.

The user accessory 108 may be configured to communicatively couple to the force sensing node 102, the portable hub 104, and/or other components of the exercise system 100. The user accessory 108 may be configured to convey information related to one or more of personal exercise, aspects of a user of the portable hub 104 (e.g., heart rate, temperature, and/or other aspects), force exerted on the force sensing node 102, information associated with the portable hub 104, and/or other information. The user accessory 108 may be physically separate and distinct from the force sensing node 102 and/or the portable hub 104. In some implementations, the user accessory 108 may include one or more of a heart rate monitor, a thermometer, a device that measures aspects of a user of the portable hub 104, a wired headset, a wireless headset, wired headphones, wireless headphones, a device that includes a display, and/or other accessories.

The external resources 110 may include sources of information, hosts and/or providers of interactive content outside of the exercise system 100, external entities participating with the exercise system 100, and/or other resources. In some implementations, some or all of the functionality attributed herein to the external resources 110 may be provided by resources included in the exercise system 100.

Figure 2:
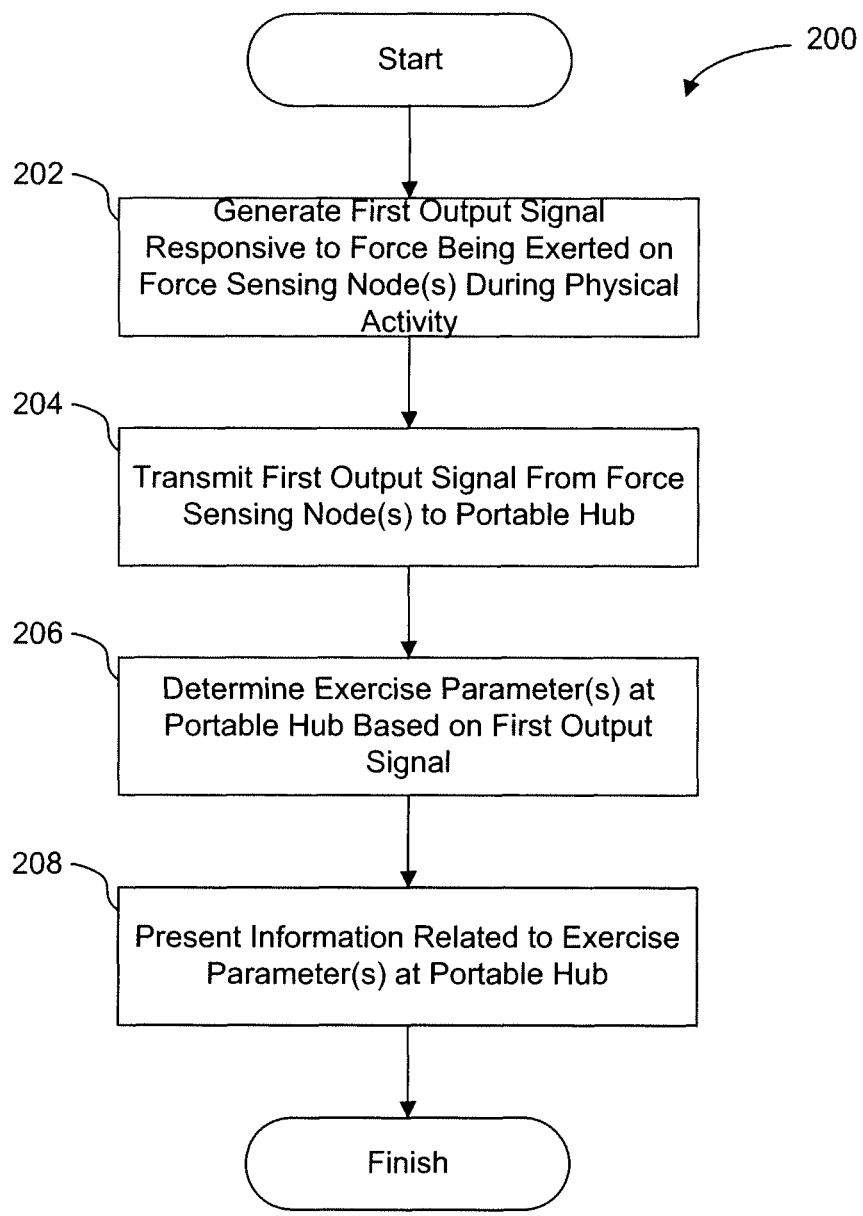
FIG. 2 illustrates a method for gathering and quantifying data related to energy expenditure during physical activity, according to one or more implementations of the invention.

FIG. 2 illustrates a method 200 for gathering and quantifying data related to energy expenditure during physical activity, according to one or more implementations of the invention. The operations of the method 200 presented below are intended to be illustrative. In some implementations, the method 200 may be accomplished with one or more additional operations not described, and/or without one or more of the operations discussed. Additionally, the order in which the operations of the method 200 are illustrated in FIG. 2 and described below is not intended to be limiting.

In some implementations, the method 200 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of the method 200 in response to instructions stored electronically on an electronic storage medium. The one or more processing devices may include one or more devices configured through hardware, firmware, and/or software to be specifically designed for execution of one or more of the operations of the method 200.

At an operation 202, a first output signal is generated responsive to force being exerted on at least one force sensing node (e.g., the force sensing node 102) during physical activity. In some implementations, the first output signal may be generated by the force sensor 112 of the force sensing node 102.

At an operation 204, the first output signal is transmitted from the at least one force sensing node (e.g., the force sensing node 102) to a portable hub (e.g., the portable hub 104). The portable hub may be physically separate and distinct from the at least one force sensing node. In some implementations, the node communications apparatus 114 may received the first output signal from the force sensor 112 and transmit the first output signal to the portable hub 104 or a component thereof (e.g., the hub communications apparatus 130).

At an operation 206, one or more exercise parameters are determined at the portable hub (e.g., the portable hub 104) based on the first output signal. In some implementations, the hub processor 146 may execute the exercise analysis module 152 to determine the one or more exercise parameters.

At an operation 208, information related to the one or more exercise parameters is presented at the portable hub (e.g., the portable hub 104). In some implementations, such information may be presented by the hub display apparatus 138 and/or the hub user interface 140. In some implementations, the information related to the one or more exercise parameters may be transmitted to and presented by the computing platform 106 rather than or in addition to being presented at the portable hub 104.

Although the invention has been described in detail for the purpose of illustration based on what is currently considered to be the most practical and preferred implementations, it is to be understood that such detail is solely for that purpose and that the invention is not limited to the disclosed implementations, but, on the contrary, is intended to cover modifications and equivalent arrangements that are within the spirit and scope of the appended claims. For example, it is to be understood that the present invention contemplates that, to the extent possible, one or more features of any implementation can be combined with one or more features of any other implementation.

What is claimed is:

1. An exercise system configured to gather and quantify data related to energy expenditure during a physical activity, the exercise system comprising:
   a plurality of force sensing nodes configured to gather data related to energy expenditure during the physical activity, the plurality of force sensing nodes being integrated into an item that is provided on at least one body part of a user, an individual force sensing node of the plurality of force sensing nodes comprising:
      at least one force sensor configured to generate a first output signal responsive to force adapted to be exerted by the at least one body part on the individual force sensing node during the physical activity;
      a node identification sensor, the node identification sensor being configured to identify the individual force sensing node and to indicate said at least one body part associated with the individual force sensing node;
      a first communications apparatus configured to transmit the first output signal;
      a node processor configured to:
         control the at least one force sensor, the node identification sensor, and the first communications apparatus;
         receive and process the first output signal for transmission by the first communications apparatus; and
         manage power for the individual force sensing node; and
   a portable hub that is physically separate and distinct from the plurality of force sensing nodes that are integrated into the item, the portable hub being configured to quantify the data related to energy expenditure during the physical activity, the portable hub comprising:
      a second communications apparatus configured to receive the first output signal from the first communications apparatus of each individual force sensing node of the plurality of force sensing nodes;
      a hub identification sensor, the hub identification sensor being configured to identify each individual force sensing node from other individual force sensing nodes of said plurality of force sensing nodes, in conjunction with the node identification sensor;
      a geo-location sensor configured to generate a second output signal related to a geo-location of the portable hub;
      a motion sensor configured to generate a third output signal related to a motion of the portable hub;
      a portable hub processor configured to execute one or more computer program modules, the one or more computer program modules comprising:
         an exercise analysis module configured to determine one or more exercise parameters based on the first output signal generated by the at least one force sensor of each individual force sensing node, the one or more exercise parameters including a magnitude of the force exerted on said individual force sensing node of the plurality of force sensing nodes by said at least one body part during the physical activity, the exercise analysis module being further configured to:
            determine the energy expenditure during the physical activity based on the magnitude of the force; and
            determine the one or more exercise parameters based on the second output signal generated by the geo-location sensor and the third output signal generated by the motion sensor;
   wherein the second communications apparatus, the geo-location sensor, the motion sensor and the portable hub processor are physically located within the portable hub.

2. The exercise system of claim 1, wherein the one or more exercise parameters further include one or more of altitude ascended during the physical activity, or comparative information associated with a prior physical activity.

3. The exercise system of claim 1, wherein the item that is provided on the at least one body part of the user is at least one wearable item such that said force adapted to be exerted by the at least one body part wearing the at least one wearable item is exerted on the plurality of force sensing nodes.

4. The exercise system of claim 3, wherein the at least one wearable item includes handwear.

5. The exercise system of claim 1, wherein the item that is provided on the at least one body part of the user is an insole, wherein the plurality of force sensing nodes are integrated into said insole, the insole configured to be received by a shoe such that said force adapted to be exerted by the bottom of a foot wearing the shoe is exerted on the plurality of force sensing nodes.

6. The exercise system of claim 1, wherein the portable hub further comprises a display apparatus configured to display, for presentation to the user, information related to the one or more exercise parameters, including (a) a force magnitude as a function of time based on the force applied on the individual force sensing node of the plurality of force sensing nodes by the at least one body part and (b) the magnitude of the force, and wherein the one or more computer program modules further comprise a display module configured to control the display apparatus to present the information including the magnitude of the force as a function of time and the force magnitude.

7. The exercise system of claim 1, wherein the portable hub further comprises a user interface configured to present user configurable settings to the user, and to receive selections from the user of values for the user configurable settings.

8. The exercise system of claim 1, wherein the portable hub further comprises a power supply, and wherein the one or more computer program modules further comprise a power management module configured to manage power delivered by the power supply.

9. The exercise system of claim 1, wherein the portable hub further comprises electronic storage configured to store information related to the one or more exercise parameters.

10. The exercise system of claim 1, wherein the one or more computer program modules comprise a clocking module configured to provide one or more functions including a clock, a timer, a stopwatch, or an occasion alarm.

11. The exercise system of claim 1, wherein the one or more computer program modules comprise a calendaring module configured to manage a calendar associated with the portable hub.

12. The exercise system of claim 1, wherein the second communications apparatus of the portable hub is further configured to transmit information related to the one or more exercise parameters.

13. The exercise system of claim 12, further comprising a computing platform that is physically separate and distinct from the plurality of force sensing nodes and the portable hub, the computing platform configured to receive and process the information related to the one or more exercise parameters transmitted by the second communications apparatus of the portable hub.

14. The exercise system of claim 1, wherein the exercise analysis module is further configured to: determine information associated with a prescribed exercise routine, the information associated with the prescribed exercise routine comprising a completion level of the prescribed exercise routine.

* * * * *